US010019078B2

(12) United States Patent
Kim et al.

(10) Patent No.: US 10,019,078 B2
(45) Date of Patent: Jul. 10, 2018

(54) DEVICE, METHOD, AND SYSTEM TO RECOGNIZE MOTION USING GRIPPED OBJECT

(71) Applicant: SAMSUNG ELECTRONICS CO., LTD., Suwon-si (KR)

(72) Inventors: Sang Joon Kim, Hwaseong-si (KR); Seung Keun Yoon, Seoul (KR); Chang Mok Choi, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/172,481

(22) Filed: Feb. 4, 2014

(65) Prior Publication Data

US 2014/0368474 A1  Dec. 18, 2014

(30) Foreign Application Priority Data

Jun. 17, 2013 (KR) ........................ 10-2013-0068870

(51) Int. Cl.
*G09G 1/00* (2006.01)
*G06F 3/0354* (2013.01)
(Continued)

(52) U.S. Cl.
CPC ........ *G06F 3/03545* (2013.01); *A61B 5/0488* (2013.01); *A61B 5/1122* (2013.01); *A61B 5/681* (2013.01); *A61B 5/6824* (2013.01); *G06K 9/00355* (2013.01); *G06K 9/00536* (2013.01); *G06K 9/222* (2013.01)

(58) Field of Classification Search
CPC . G06F 3/03; G06F 3/01; G06F 3/0354; G06F 3/017
See application file for complete search history.

(56) References Cited

U.S. PATENT DOCUMENTS 6,380,923 B1  4/2002 Fukumoto et al.
2002/0145596 A1  10/2002 Vardi
(Continued)

FOREIGN PATENT DOCUMENTS

CN  1531676 A  9/2004
CN  1625766 A  6/2005
(Continued)

OTHER PUBLICATIONS

Extended European Search Report dated Oct. 28, 2014 in corresponding European application No. 14160869.5 (6 pages in English).
(Continued)

*Primary Examiner* — Michael Faragalla
(74) *Attorney, Agent, or Firm* — NSIP Law

(57) ABSTRACT

A device, a method, and a system recognize a motion using a gripped object. The motion recognition device may estimate a state of a wrist of a user according to a writing action using the gripped object and may estimate a joint motion of a body part related to the wrist according to the writing action. The device may then estimate a state of the gripped object according to the state of the wrist and the joint motion. Additionally, the motion recognition device may control an external device by using a control signal generated by continuously tracking the state of the object.

33 Claims, 14 Drawing Sheets

(51) Int. Cl.
  *A61B 5/0488* (2006.01)
  *A61B 5/11* (2006.01)
  *A61B 5/00* (2006.01)
  *G06K 9/00* (2006.01)
  *G06K 9/22* (2006.01)

(56) References Cited

U.S. PATENT DOCUMENTS

| | | | |
|---|---|---|---|
| 2006/0121958 A1 | 6/2006 | Jung et al. | |
| 2009/0267896 A1 | 10/2009 | Hiramatsu | |
| 2009/0281594 A1* | 11/2009 | King | A61N 1/36071 607/46 |
| 2010/0030343 A1* | 2/2010 | Hansen | A61F 2/6607 623/47 |
| 2010/0066664 A1 | 3/2010 | Son et al. | |
| 2010/0251454 A1* | 10/2010 | Kiernan | A41D 1/002 2/69 |
| 2011/0012759 A1* | 1/2011 | Yin | A61B 5/1118 341/20 |
| 2011/0054360 A1 | 3/2011 | Son et al. | |
| 2011/0118621 A1* | 5/2011 | Chu | A61B 5/0488 600/546 |
| 2011/0298709 A1* | 12/2011 | Vaganov | G06F 3/03546 345/158 |
| 2012/0075206 A1* | 3/2012 | Yuzawa | G06F 3/011 345/173 |
| 2012/0172682 A1* | 7/2012 | Linderman | A61B 5/0476 600/301 |
| 2012/0221177 A1 | 8/2012 | Shin et al. | |
| 2012/0235899 A1 | 9/2012 | Han et al. | |
| 2012/0319940 A1 | 12/2012 | Bress et al. | |
| 2013/0045774 A1* | 2/2013 | Arat | G06F 1/1694 455/556.1 |
| 2014/0194726 A1* | 7/2014 | Mishelevich | A61N 7/00 600/411 |
| 2014/0200432 A1* | 7/2014 | Banerji | A61B 5/0488 600/383 |
| 2014/0267024 A1* | 9/2014 | Keller | G06F 3/017 345/156 |

FOREIGN PATENT DOCUMENTS

| | | |
|---|---|---|
| JP | 06-039754 A | 2/1994 |
| JP | 7-28593 A | 1/1995 |
| JP | 11-338597 A | 12/1999 |
| JP | 2005-352739 A | 12/2005 |
| JP | 2008-305199 A | 12/2008 |
| JP | 2009-522631 A | 6/2009 |
| JP | 2009-217733 A | 9/2009 |
| JP | 2012-73830 A | 4/2012 |
| KR | 10-2011-0040165 A | 4/2011 |
| KR | 10-2011-0137587 | 12/2011 |
| KR | 10-2012-0133351 | 12/2012 |

OTHER PUBLICATIONS

Japanese Office Action dated Oct. 3, 2017, Counterpart of Japanese Application No. 2014-23149, (4 pages Japanese, 4 pages in English).

Chinese Office Action dated Dec. 7, 2017 in corresponding Chinese Application No. 2014-10141577.4 (5 pages in English, 5 pages in Chinese).

Japanese Office Action dated Jan. 16, 2018 in corresponding Japanese Application No. 2014-023149 (4 pages in English, 6 pages in Japanese).

* cited by examiner

DEVICE, METHOD, AND SYSTEM TO RECOGNIZE MOTION USING GRIPPED OBJECT

CROSS-REFERENCE TO RELATED APPLICATION(S)

This application claims the benefit under 35 USC § 119(a) of Korean Patent Application No. 10-2013-0068870, filed on Jun. 17, 2013, in the Korean Intellectual Property Office, the entire disclosure of which is incorporated herein by reference for all purposes.

BACKGROUND

1. Field

The following description relates to a device and method to recognize a user motion.

2. Description of Related Art

Recently, the use of various portable electronic devices such as a smart phone, a tablet, a personal computer (PC), and a personal digital assistant (PDA) is increasing.

According to a general technology that analyzes a motion of a human body, the motion is tracked by attaching an acceleration sensor to a device to sense motion of the human body and the data produced by the acceleration sensor is interpreted. Such a technology is effective when analyzing a simple motion, without the need to accurately detect a motion of the human body.

Another general technology to analyze the motion of the human body includes analyzing image information obtained from a motion sensing camera attached to the motion sensing device. In this case, it is presumed that a user is in front of the motion sensing device. Therefore, the user needs to manage his or her position with respect to the device. In addition, analysis of the motion of the user may be more accurately performed when body parts of the user do not overlap.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method for recognizing a motion performed using a gripped object includes estimating a state of a wrist of a user according to a writing action performed using the gripped object, estimating a joint motion of a body part of the user related to the wrist according to the writing action, and estimating a state of the gripped object according to the state of the wrist and the joint motion.

The method may further include generating a control signal for controlling an external device by continuously tracking the state of the gripped object.

The method may further include detecting a start of the writing action of the user using the gripped object.

The detecting may include determining that the writing action has started when at least one of a sound generated by the writing action and a grip of an object corresponding to writing is detected.

The estimating of the state of the gripped object may include estimating a contact position of the gripped object with respect to a ground surface according to the state of the wrist and the joint motion.

The estimating of the state of the wrist may include detecting an acceleration according to the writing action, and estimating the state of the wrist according to the acceleration.

The estimating of the joint motion may include detecting electromyogram (EMG) information of the body part related to the wrist according to the writing action, and estimating the joint motion according to the EMG information.

The method may further include detecting a biomedical signal corresponding to the user, and compensating for errors in the estimated state of the object, using a motion artifact according to the biomedical signal.

The method may further include storing a shape generated by continuously tracking the state of the gripped object.

The estimating of the joint motion may include estimating a strength of a force exerted by the user for gripping the gripped object, and the estimating of the joint motion may further include generating the shape in a thickness corresponding to the strength of the force by continuously tracking the state of the gripped object.

The method may further include identifying a type of the gripped object, and performing an action according to the type of the gripped object by continuously tracking the state of the object.

In another general aspect, a device for recognizing a motion performed using a gripped object includes a wrist state estimator configured to estimate a state of a wrist according to a writing action performed using the gripped object, a joint motion estimator configured to estimate a joint motion of a body part of the user related to the wrist according to the writing action, and an object state estimator configured to estimate a state of the gripped object according to the state of the wrist and the joint motion.

The device may further include a signal generator configured to generate a control signal for controlling an external device by continuously tracking the state of the gripped object.

The device may further include an action start detector configured to detect a start of the writing action of the user using the gripped object.

The action start detector may include an action start determiner configured to determine that the writing action has started when at least one of a sound generated by the writing action and a grip of an object corresponding to writing is detected.

The object state estimator may include a ground surface contact estimator configured to estimate a contact position of the gripped object with respect to a ground surface according to the state of the wrist and the joint motion.

The wrist state estimator may include an acceleration detector configured to detect acceleration with respect to six axes according to the writing action using the gripped object, and estimate the state of the wrist including at least one of a position change of the wrist and a rotation of the wrist according to the acceleration.

The joint motion estimator may include an electromyogram (EMG) detector configured to detect EMG information generated at the body part related to the wrist according to the writing action; and estimates the joint motion according to the EMG information.

The device may further include a biomedical signal detector configured to detect a biomedical signal corresponding to the user, and an object state compensator configured to compensate for errors in the estimated state of the object, using a motion artifact according to the biomedical signal.

The device may further include a writing generator configured to generate a shape generated by continuously tracking the state of the gripped object.

The device may provide that the joint motion estimator includes a gripped strength estimator configured to estimate a strength of a force exerted by the user for gripping the object, and the writing generator is configured to generate the shape in a thickness corresponding to the strength of the force by continuously tracking the state of the gripped object.

The writing generator may include an object identifier configured to identify the type of the object using at least one of an object gripping position, a sound generated by the writing action and, a voice of the user, and generates the shape by performing the action corresponding to the type of the object.

In another general aspect, a system for recognizing a motion using a gripped object includes a motion recognition device configured to estimate a state of a gripped object according to a state of a wrist of a user and a joint motion of a body part related to the wrist, and configured to transmit a control signal for controlling an external device, the control signal generated by continuously tracking the state of the gripped object and the external device configured to perform a predetermined operation corresponding to the control signal when receiving the control signal.

The motion recognition device may select an external device corresponding to a shape generated by continuously tracking the state of the gripped object, and may generate a signal for controlling the selected external device as the control signal.

The control signal may include a control command instructing the external device to perform an operation corresponding to a predetermined part of the external device when a user action that activates the predetermined part is detected from the shape.

In another aspect, a method for recognizing a motion using a gripped object includes estimating a state of a gripped object according to a state of a wrist of a user and a joint motion of a body part related to the wrist, storing a shape generated by continuously tracking the state of the gripped object, recognizing the shape to identify an external device corresponding to the shape and to determine an operation to be performed by the external device, and transmitting a control signal to the external device to instruct the external device to perform the operation.

The shape may include written language and the recognizing may include recognizing the written language.

The external device may be identified based on the recognized written language.

The operation to be performed by the external device may be determined based on the recognized written language The external device may be identified based on recognizing that the shape represents the external device.

A region of the shape may be a drawing of a portion of the represented external device that performs a designated operation, and the method may further include, when the user selects the portion, the transmitting the control signal to instruct the external device to perform the designated operation.

Other features and aspects will be apparent from the following detailed description, the drawings, and the claims.

Figure 1:
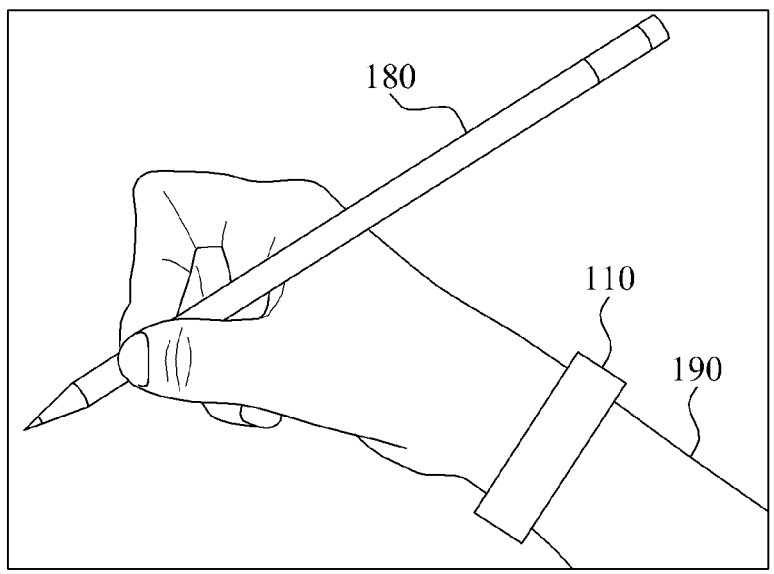
FIG. 1 is a diagram illustrating a motion recognition device to recognize a motion of a gripped object, according to an example embodiment.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

A user interface (UI) of a mobile device including a touch-based input unit is configured to recognize user inputs received at a keyboard that senses a user touch. To use such an input unit, the user would need to learn a specific way of using the touch-based keyboard. However, such a way of using the touch-based keyboard may not be intuitive. In addition, in view of a trend towards a reduction in size of existing mobile devices, such as a wearable device that is small in size, it may be difficult for the user to control the mobile device using the touch-based input unit.

Hereinafter, embodiments will be described with reference to the accompanying drawings.

FIG. 1 is a diagram illustrating a motion recognition device 110 to recognize a motion of a gripped object, according to an example embodiment. The motion recognition device 110 estimates a state of a gripped object 180 gripped by a user 190. For example, the motion recognition device 110 recognizes contents the user 190 writes using the gripped object 180, by continuously tracking the state of the gripped object 180. In the following description, writing denotes a user action of writing or drawing contents using the gripped object 180 and actions including drawing letters, words, sentences, numbers, and drawings.

According to an embodiment, the motion recognition device 110 is attached to a user 190. For example, the motion recognition device may be attached to the user 190 at a wrist. The motion recognition device 110 includes at least one sensor to detect at least one signal, such as a motion signal, a biomedical signal, or another type of signal. The motion recognition device 110 accurately estimates motions of body parts of the user 190 such as a hand, a wrist, an arm, and the like, by combining various types of a biomedical signal and a motion signal that are detected. The motion recognition device 110 may store information about contents, which are freely and intuitively written on a note or other medium, using the gripped object 180, into readable data based on the written contents. Alternatively, the contents may be stored in an external device, in communication with the motion recognition device 110 to act as an external data repository. For instance, as the motion recognition device 110 recognizes and estimates the motions from the user 190, the motion recognition device 110 wired or wirelessly transmits data indicative of the motions to the external device, and the external device stores the data for future use.

In one example, the gripped object 180 refers to a tool that the user 190 uses to write certain contents. For example, the gripped object 180 may be a pen, a pencil, a stylus pen, a writing brush, or another object in a shape that is comfortable and enables the user 190 to grip the object. As discussed above, contents refer to the substance of what is written using the gripped object 180. The grippable shape may include an elongated shape, such as a chopstick. The gripped object 180 is configured to have a pointed end that is manipulated by the user 190, such that the movement of the pointed end of the gripped object 180 is recorded and the recorded movement generates the contents.

Figure 2:
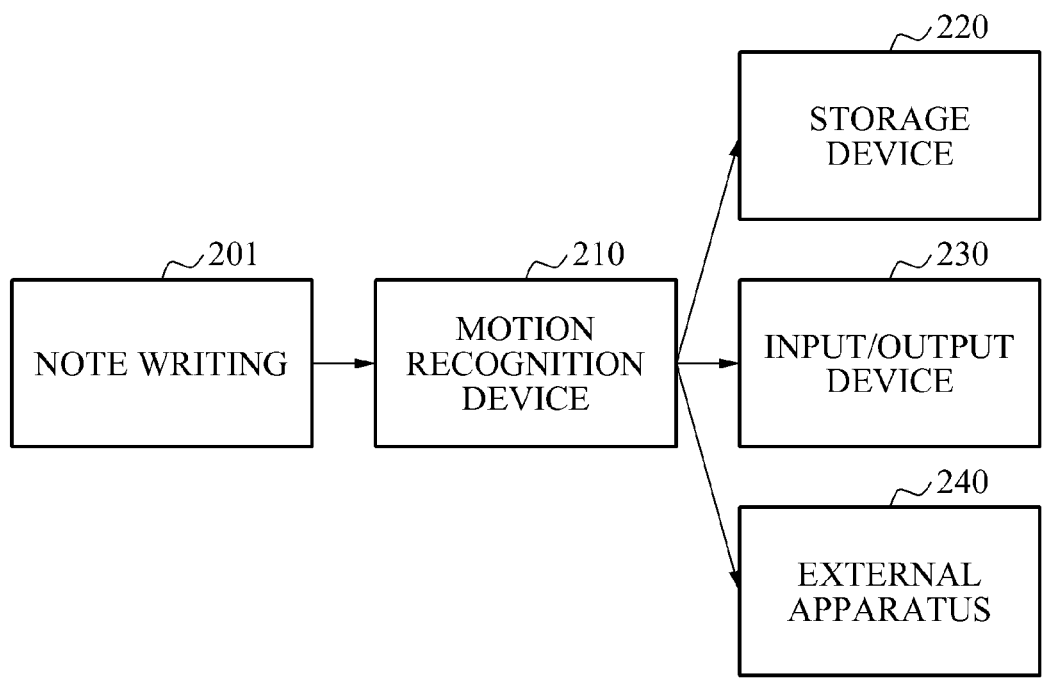
FIG. 2 is a diagram illustrating a configuration of a system to recognize a motion of the gripped object, according to an example embodiment.

FIG. 2 is a diagram illustrating a configuration of a system to recognize a motion of the gripped object, according to an example embodiment. The motion recognition system includes a motion recognition device 210, a storage device 220, an input and output device 230, and an external apparatus 240. Although labeled as an external apparatus 240, in one configuration, this apparatus may be integrated into the system. Furthermore, although FIG. 2 illustrates the storage device 200, the input/output device 230, and the external apparatus 240 to be external to the motion recognition device 210, either all or at least one of the storage device 220, the input/output device 230, and the external apparatus 240 may be integrated into or part of the motion recognition device 210.

When a user 190 wearing the motion recognition device 210, according to an embodiment, writes down something on a note, the motion recognition device 210 recognizes a note being written from the note writing 201. For example, the user 190 performs note writing 201 using gripped object 180. The motion recognition device 210 stores the note writing 201 in the storage device 220, transmits the note writing 201 to the input/output device 230, or controls the external apparatus 240 based on the note writing 201. A method of recognizing and utilizing the note writing 201 of the user 190 by the motion recognition device 210 will be described further with reference to FIGS. 3 to 12.

Figure 3:
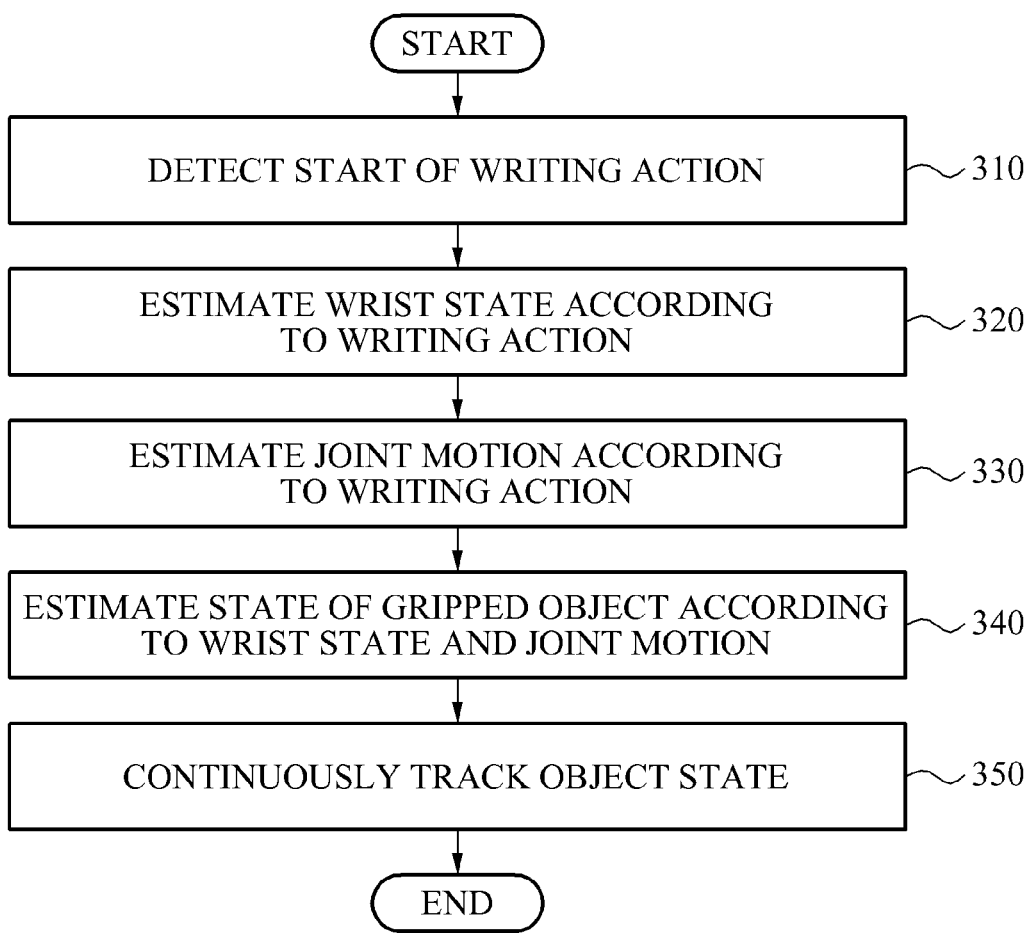
FIG. 3 is a flowchart illustrating a method to recognize a motion of the gripped object, according to an example embodiment.

FIG. 3 is a flowchart illustrating a method to recognize a motion of the gripped object, according to an example embodiment. The method includes operations that may be performed by a sensor and a processor included in a motion recognition device 210.

At operation 310, the method detects a start of a writing action. For example, motion recognition device 210 detects the start of the writing action. According to an embodiment, operation 310 may determine that the writing action has started when at least one of a sound produced from the writing action and information about a grip of an object is detected. For example, the sound generated by the writing action includes a frictional sound between the gripped object and a contacting surface, such as a ground surface or a paper surface. In the context of this application, a "ground surface" is used as a generic term to refer to a surface with which the gripped object may make contact with to write upon the surface. As just noted, the writing may be performed on a paper surface, but other appropriate planar surfaces are used in other embodiments. Operation 310 interprets the frictional sound as indicating that the writing action has begun. In addition, when a particular hand position of the user, for example, a pen gripping position, is detected, at operation 310, the method determines that the writing action has started. The writing action may include a writing motion of the user using the gripped object.

At operation 320, the method estimates a state of a wrist according to the writing action. The state of the wrist may include a wrist position, a wrist position change, a rotation angle, and a rotational direction. Because the user 190 moves his or her wrist as the writing action occurs, information about how the wrist moves provides information about how the gripped object 180 is manipulated, which can help deduce the writing motion. For example, the method of the motion recognition device estimates a relative change in position of the wrist by detecting acceleration using an acceleration sensor according to the writing action. When the acceleration sensor is capable of detecting six-axis acceleration, the rotation angle and the rotational direction of the wrist may be estimated.

At operation 330, the method estimates a joint motion according to the writing action. The joint motion may include a joint motion of a body part related to the wrist. For example, the joint motion may include a motion of bending a finger or an arm. In one embodiment, the motion recognition device detects an electromyogram (EMG) of the body part corresponding to the wrist that performs the writing action, and estimates the joint motion according to contraction and relaxation signals of muscles included in the EMG. For example, the body part related to the wrist may be one of a finger joint, a wrist joint, an arm joint, and a shoulder joint. However, the body part related to the wrist is not limited to these examples, and EMG data may be derived from other body parts.

At operation 340, the method estimates a state of the gripped object according to the state of the wrist estimated at operation 320 and the joint motion estimated at operation 330. The state of the gripped object may include one or more of a position of the gripped object, a contact position between the gripped object and a ground surface, a gradient of the gripped object, calculated based on the position of the gripped object, a pressure degree of the gripped object, and other information about the positioning and movement of the gripped object, according to a gripping position and motion of the user with respect to the gripped object. For example, the motion recognition device may estimate the contact position between the gripped object and the ground surface, according to the state of the wrist and the joint motion.

According to an embodiment, the motion recognition device compensates for errors in the estimated state of the gripped object, by detecting a biomedical signal of the user and using a motion artifact according to the biomedical signal to compensate for inaccuracies in the estimated state of the gripped object. The compensation using the motion artifact will be described further with reference to FIG. 11.

At operation 350, the method continuously tracks the state of the gripped object. The motion recognition device generates a control signal for controlling the external apparatus by continuously tracking the state of the gripped object, or by storing a shape generated by continuously tracking the state of the gripped object. For example, the shape generated by continuously tracking the state of the gripped object may be stored or used as computer-readable data. By tracking the state of the gripped object, the method provides information that indicates which content the user intends to write using the gripped object.

In one example, the shape generated by continuously tracking the state of the gripped object is obtained by recognizing contents written by the user using the gripped object, by the motion recognition device 210. As aforementioned, the shape generated by continuously tracking the state of the gripped object 180 may include a result of recognizing letters, words, sentences, numbers and drawings drawn by the user.

Figure 4:
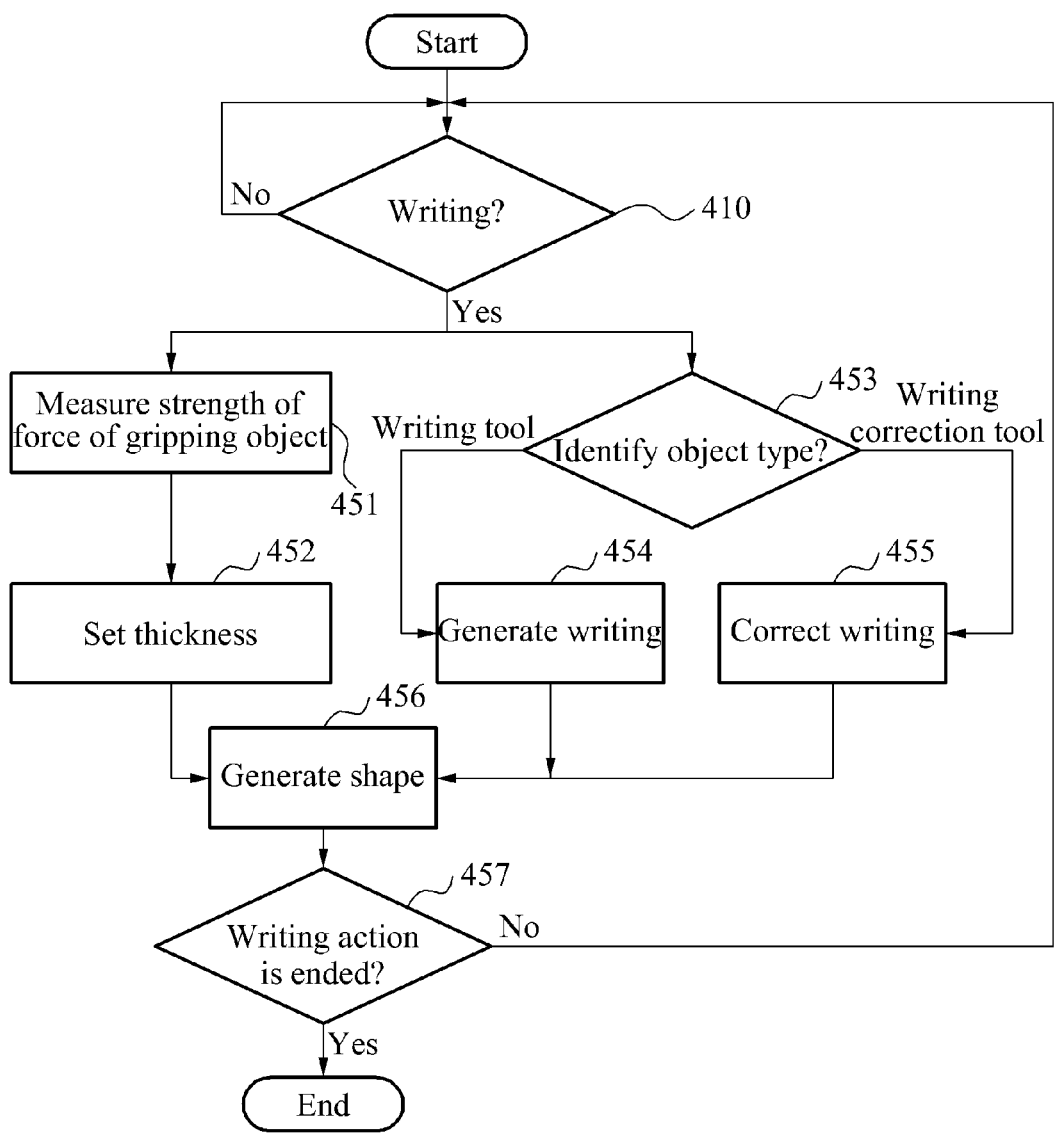
FIG. 4 is a flowchart illustrating a method to continuously track a state of the gripped object by recognizing a motion using the gripped object, according to an example embodiment.

FIG. 4 is a flowchart illustrating a method to continuously track a state of the gripped object by recognizing a motion using the gripped object, according to an example embodiment.

At operation 410, the method determines whether a user is writing using an object. In an embodiment, the object is the gripped object 180. Whether the user is writing using the object may be determined by whether a writing action has started as shown in FIG. 3 and discussed with respect to FIG. 3, above. For example, the method may determine that the writing action has started when at least one of a sound generated by the writing action and grip information of an object indicating a writing action is detected. When the user is determined to be not writing, the motion recognition device may wait until the writing action starts to track the motion of the gripped object 180.

At operation 451, the method measures strength of a force of the user for gripping the object. The motion recognition device estimates the strength of the force of the user for gripping the object, from a joint motion of a body part related to a wrist. The force measured by operation 451 is the force exerted by parts of the user's hand that provide a grip upon the gripped object 180 by the user 190 squeezing the gripped object 180. For example, the motion recognition device may detect an EMG signal received from muscles, generated when the user bends his or her finger to grip the object, thereby estimating the strength of the force from intensity of the EMG signal.

Next, at operation 452, the method sets thickness. The thickness refers to the thickness of the footprint resulting from the contact between the gripped object 180 and the surface that it writes upon. In example embodiments, the thickness includes a thickness of a letter written by the user, a thickness of a line drawn by the user, a range of a portion erased by an eraser, and an effective range of a writing correction tool. For example, in 452, the motion recognition device sets thickness corresponding to the strength of the force estimated in 451, and applies the thickness to the letter, the line, and the ranges as just discussed. For example, as the estimated strength of the force is greater, the thickness may be increased in proportion to the strength. In certain embodiments, the writing correction tool includes an eraser erasing written contents and/or a brush applying a brush effect.

At operation 453, the method identifies a type of the object gripped by the user. For example, the motion recognition device identifies the type of the gripped object using at least one of a gripping position of the user with respect to the gripped object and the sound generated by a writing action. The type of the gripped object corresponds to its overall shape and method of use. A method of identifying the type of the gripped object will be described further later.

According to an embodiment, the motion recognition device identifies a type of the gripped object using a position of the user gripping the gripped object. For example, when the user grips an elongated object such as a pen, the motion recognition device identifies the gripped object as a writing tool. When the user grips a thick object such as an eraser, the motion recognition device identifies the gripped object as an erasing tool. However, not limited to the foregoing examples, the motion recognition device may identify the type of the gripped object as a tool corresponding to a position of the user according to a unique shape of the gripped object. For example, gripped objects that are contoured or held in different ways may be recognized as belong to specific types of gripped objects.

According to another embodiment, the motion recognition device identifies the type of the gripped object, using the sound generated by the writing action. In an embodiment, the sound generated by the writing action is a frictional sound between the gripped object and a contacting surface such as a ground surface or a paper surface. The sound is analyzed to identify the appropriate type of the gripped object. In an example, when the frictional sound is quick and often, the gripped object is identified as the erasing tool. When the frictional sound is slow and infrequent, the gripped object is identified as a writing tool. Such an approach may be implemented by tracking how many sounds occur during a given time period or otherwise tracking the speed and frequency of the frictional sounds. Additionally, the frictional sounds may be interpreted differently in other embodiments. For example, there may be thresholds or metrics that are used to establish if the gripped object should be considered a writing tool or an eraser.

As another example, the motion recognition device measures a waveform of the frictional sound between the gripped object and the contact surface, thereby determining that an object of a type corresponding to the waveform is gripped by the user. Such a waveform, when measures, characterizes the frictional sounds so that they may be identified based on signal analysis.

For example, the motion recognition device stores, in advance of receiving the waveform to be classified, a waveform of a frictional sound generated between a writing tool and a paper surface, and a waveform of a frictional sound generated between an eraser and a paper surface. The motion recognition device identifies the type of the gripped object, by comparing the frictional sound generated between the gripped object and the paper surface with the stored waveform. Based on the comparison, the motion recognition device classifies the gripped object as being a writing tool or an eraser. For example, the classification may be based on which preexisting waveform is most similar to the waveform produced using the gripped object.

As yet another example, the motion recognition device identifies the type of the gripped object by recognizing a voice selection of the user. In an example, when the user says "red", the motion recognition device identifies the gripped object as a "red pen" by recognizing the voice of the user. However, the gripped object may not always correspond to a result of voice recognition, in that sometimes the voice recognition command is directed towards other input variables than. For example, even while writing with a black pen, the user may freely change colors by having the motion recognition device recognize colors by voice. Thus, if the user is writing with a black pen, if the user says "blue" it may simply indicate a color change for the pen. However, if the user is erasing, if the user says "blue" it may lead to a color change for the pen as well as a change from eraser to pen object type.

Next, at operation 454, when the gripped object is identified as a writing tool such as a pencil, the method generates writing. In a similar manner to FIG. 3, the motion recognition device generates writing by continuously tracking the state of the gripped object. Here, the motion recognition device generates writing according to the thickness set in 452.

At operation 455, when the gripped object is identified as the writing correction tool such as an eraser, the method corrects writing. In a similar manner to FIG. 3, the motion recognition device corrects writing by continuously tracking the state of the gripped object. Here, the motion recognition device corrects writing according to the thickness set in 452.

Next, at operation 456, the method generates a shape corresponding to the writing of the user, by performing an action according to the identified type of the gripped object. For example, the shape is generated based on the writing generated and corrected according to operations 452, 454, and 455. For example, by varying the thickness of the line according to the strength of the force of gripping the gripped object, the motion recognition device may generate a shape corresponding to the writing performed by the user, written in a color corresponding to a voice recognition input.

At operation 457, the method determines whether the user has ended the writing. For example, when the user is not gripping the gripped object any more, when a position for gripping an gripped object is not for writing, when the frictional sound between the gripped object and the contact surface is not detected for a predetermined time, and the like, it is determined that the writing is ended. However, other events may cause an embodiment to determine that the user has ended the writing, and thus, the examples above are merely meant as illustrative examples. According to an embodiment, when it is determined that the writing is ended, motion recognition may be ended and thus, the position of the gripped object is no longer tracked. Alternatively, when it is determined that the writing is not ended, the method returns to operation 410 to reinitiate the process of tracking writing.

Figure 5:
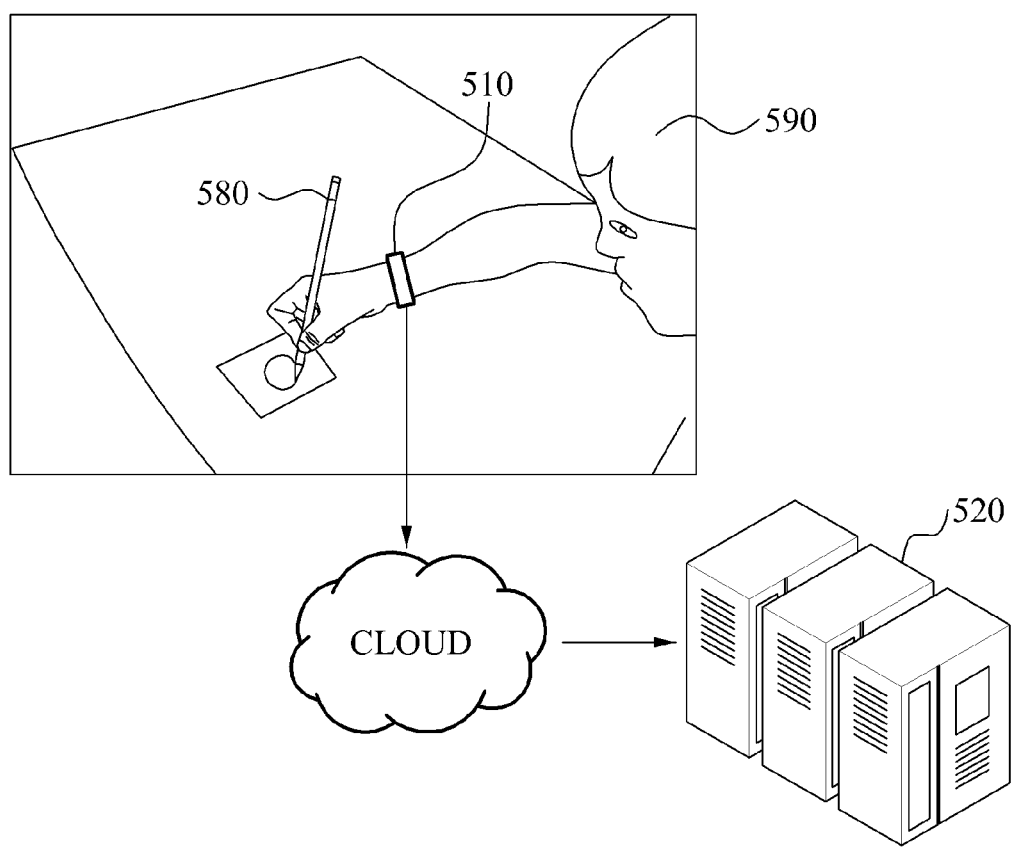
FIG. 5 is a diagram illustrating an operation for storing a recognition result from a motion recognition device for recognizing a motion using the gripped object, according to an example embodiment.

FIG. 5 is a diagram illustrating an operation of storing a recognition result from a motion recognition device 510 for recognizing a motion using a gripped object, according to an example embodiment. As shown in FIG. 5, when a user 590 writes particular contents, the motion recognition device 510 may store a shape generated by continuously tracking a state of a gripped object 580.

According to an embodiment, the motion recognition device 510 may store the shape in a storage device using a communication network, a cloud service or alternative remote or local storage solutions. In an example embodiment, the storage device includes a server 520. The server 520 may host the remote storage.

Figure 6:
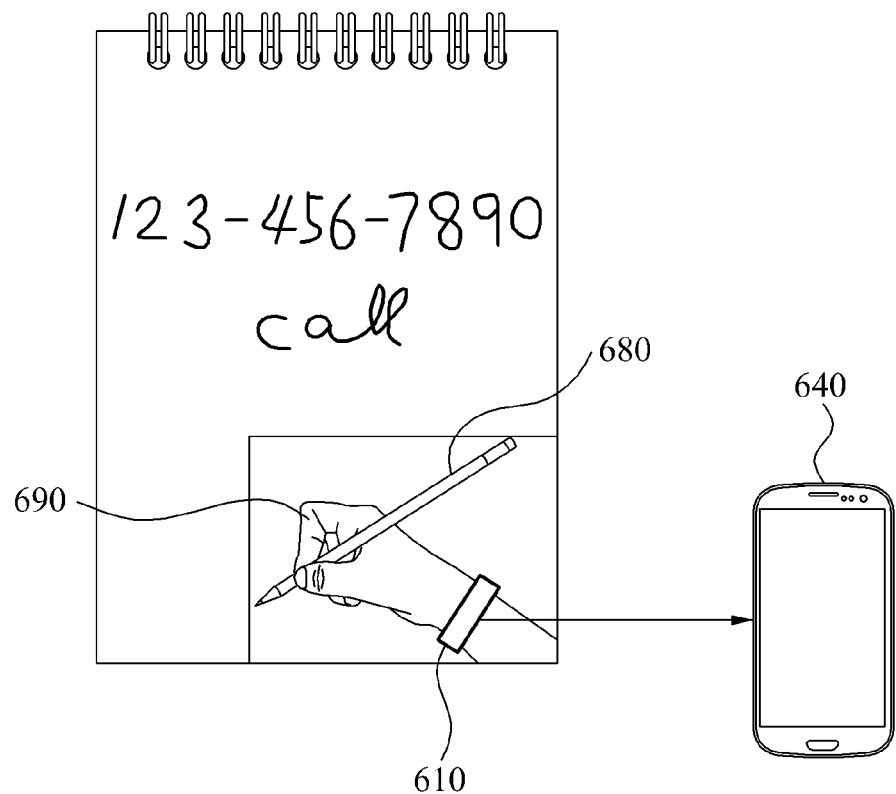
FIGS. 6, 7, and 8A to 8B are diagrams illustrating operations to control an external apparatus using a motion recognition device to recognize a motion using the gripped object, according to example embodiments.

FIG. 6 is a diagram illustrating an operation of controlling an external apparatus 640 by using a motion recognition device 610 to recognize a motion using a gripped object 680, according to an example embodiment. The motion recognition device 610 transmits a control signal for controlling the external apparatus 640. The control signal is generated by continuously tracking a state of the gripped object 680. When receiving the control signal, the external apparatus 640 performs a predetermined operation.

For example, a user 690 wearing the motion recognition device 610 may write contents including a phone number, for example 123-456-7890 and "call", using the gripped object 680. By tracking the movement of the gripped object 680, the motion recognition device 610 is able to recognize that the contents of what the user has written is that string of digits, including hyphens and the command, "call." Based on this recognition, the motion recognition device 610 establishes that the user's intend is to "call" the above-listed phone number. Therefore, the motion recognition device 610 wirelessly transmits a control signal, including a command to call the written phone number, to the external apparatus 640 connected in advance, such as a smart phone. When receiving the control signal, the external apparatus 640 may make a call to the phone number. Thus, this example illustrates that the contents of what the user writes potentially has meaning. In various examples, the contents are recognized as providing input, or may also be recognized as providing commands to be implemented at the external apparatus 640.

As another example, the motion recognition device 610 may simply transmit the raw shape generated by continuously tracking the state of the gripped object 680 to an input/output device, using a wired or wireless connection. In an embodiment, the input/output device displays the transmitted shape.

Figure 7:
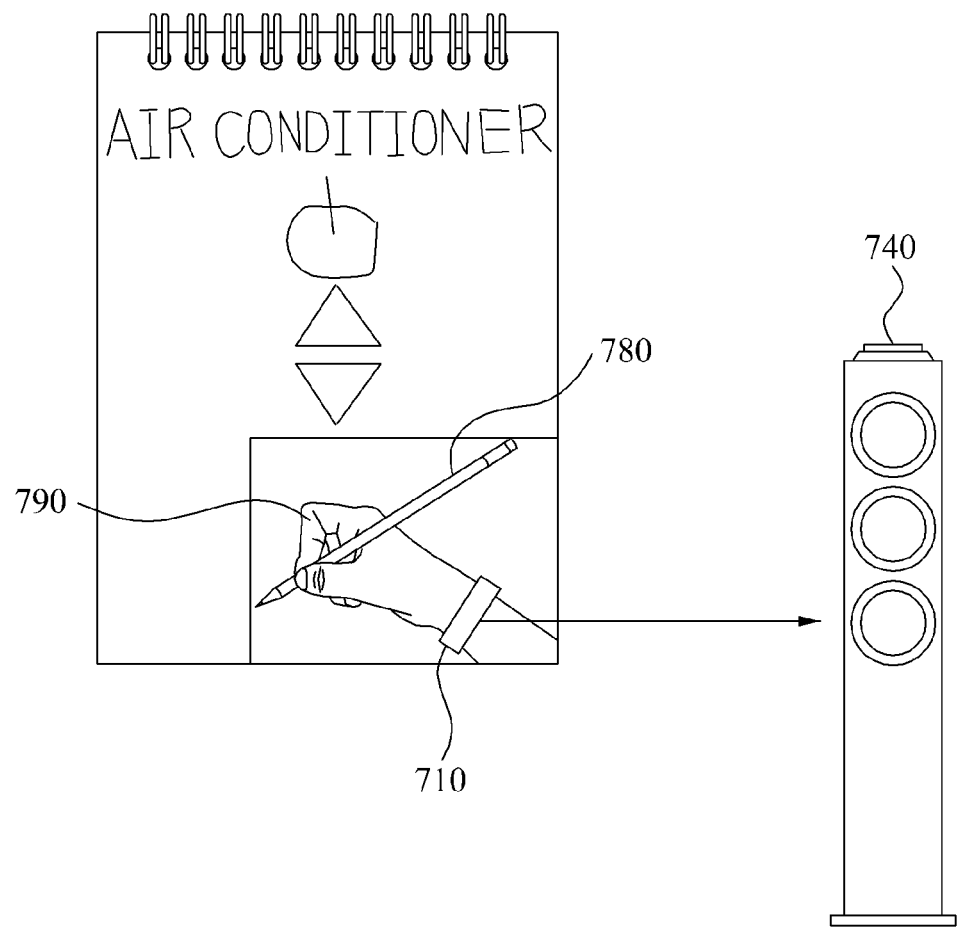

FIG. 7 is a diagram illustrating another operation of controlling an external apparatus 740 by using a motion recognition device 710 to recognize a motion using the gripped object 780, according to an example embodiment. The motion recognition device 710 may select the external apparatus 740 corresponding to a shape generated by continuously tracking a state of the gripped object 780, and generate a control signal for controlling the external apparatus 740. Here, the shape generated by continuously tracking the state of the gripped object 780 may include a name, a shape, and the like of the external apparatus 740. Thus, if the shape generated by continuously tracking the state of the gripped object 780 contains words or illustrations that match the external apparatus 740, the shape may be used to establish which external apparatus 740 to identify as the external apparatus 740 to be controlled.

For example, when a user 790 wearing the motion recognition device 710 writes the name of the external apparatus 740, for example "air conditioner," using the gripped object 780 as shown in FIG. 7, and draws a remote controller button, the motion recognition device 710 selects the external apparatus 740 corresponding to the written name, and controls the external apparatus 740. Here, as shown in FIG.

7, the motion recognition device 710 recognizes writing corresponding to a remote controller of the "air conditioner" and thereby controls a cooling temperature setting of the air conditioner. According to an embodiment, when the user 790 taps a portion corresponding to the remote controller button, the motion recognition device 710 may detect the tapping and generate a control signal for controlling the cooling temperature of the "air conditioner," which is the external apparatus 740 in this example.

Figure 8A:
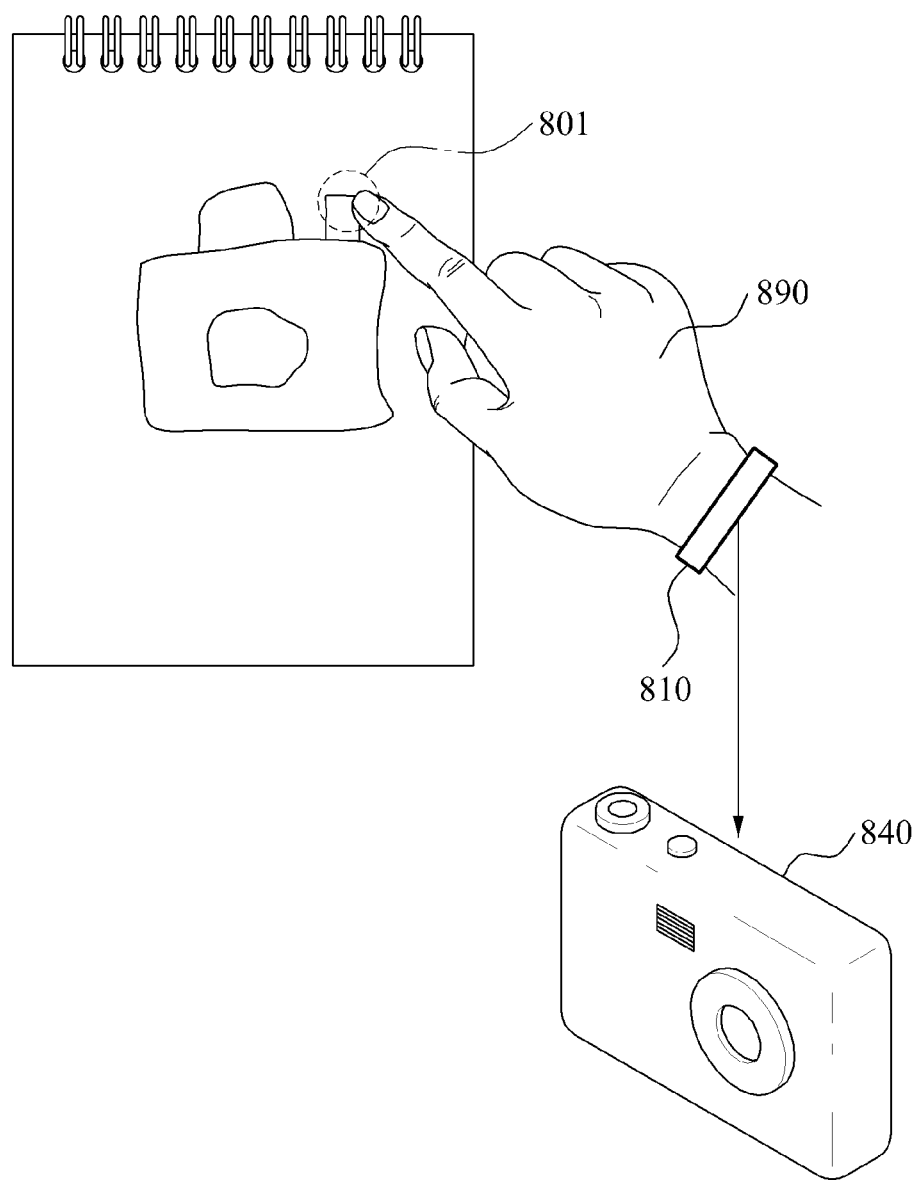
Figure 8B:
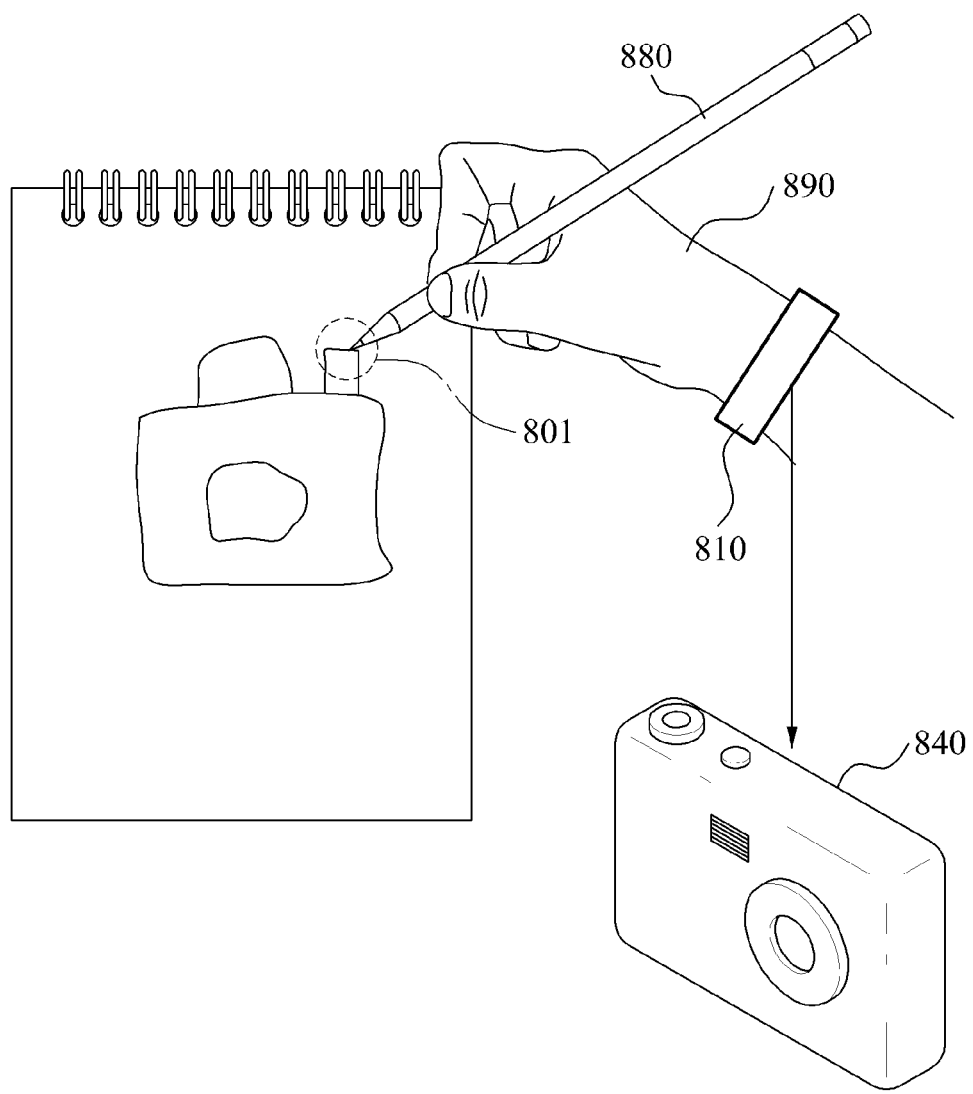

FIGS. 8A and 8B are diagrams illustrating yet another operation of controlling an external apparatus 840 by using a motion recognition device 810 to recognize a motion using a gripped object, according to an example embodiment. The motion recognition device 810 may generate a control signal for controlling the external apparatus 840, corresponding to a shape generated by continuously tracking a state of the gripped object. FIG. 8A does not illustrate the gripped object, but instead illustrates a situation where the shape has already been drawn, in a manner similar to that discussed above. According to an embodiment, the control signal may control the external apparatus 840 to perform an action corresponding to a predetermined part 801 when a user action activating the predetermined part 801 is detected from the shape generated by continuously tracking the state of the gripped object. Here, the predetermined part 801 may include a spot corresponding to a particular coordinate in the shape. The motion recognition device 810 may recognize, based on the nature of the shape and the relationship between the remainder of the shape and the predetermined part 801, that the predetermined part 801 inherently includes certain functionality.

For example, a user 890 wearing the motion recognition device 810 writes a shape corresponding to the external apparatus 840 using the gripped object as shown in FIGS. 8A and 8B. In FIG. 8, this shape is a drawing of a camera, which is the external apparatus 840.

In this case, when the motion recognition device 810 detects a user action, for example a tapping motion, which activates the predetermined part 801, for example a shutter, from the written shape, the motion recognition device 810 may generate a control signal commanding to perform a corresponding operation, for example photographing. For example, the user action may include a tapping motion by which the user taps the predetermined part 801 with his or her finger as shown in FIG. 8A and a tapping motion by which the user taps the predetermined part 801 using a gripped object 880 as shown in FIG. 8B.

When receiving the control signal, the external apparatus 840, for example a camera, may perform the predetermined operation, that is, obtaining a photographic image.

Figure 9A:
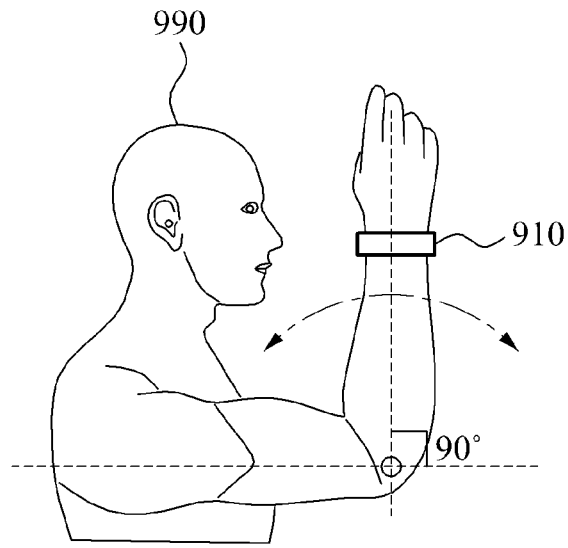
FIGS. 9A to 9B are diagrams illustrating a motion recognition device that detects a spatial motion to recognize a motion using the gripped object, according to an example embodiment.
Figure 9B:
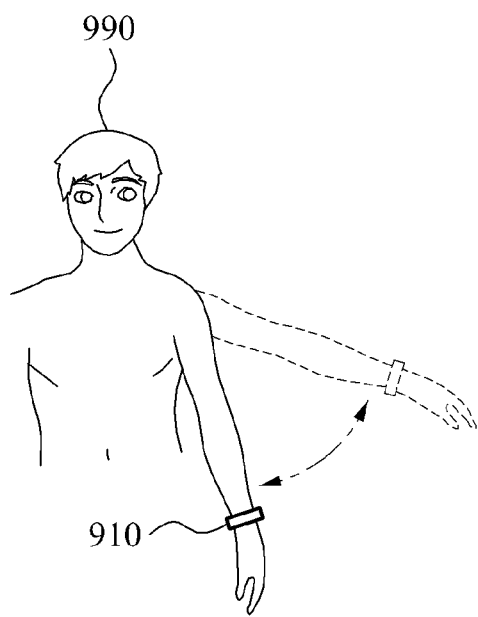

FIGS. 9A to 9B are diagrams illustrating a motion recognition device 910 that detects a spatial motion to recognize a motion using the gripped object, according to an example embodiment. The motion recognition device 910 worn on a user 990 may estimate information related to a state of a wrist of the user including a spatial motion of the wrist, using an acceleration signal detected by an acceleration sensing unit. The motion recognition device 910 may be situated on either wrist of the user 990, but in one embodiment the motion recognition device 910 is situated on the wrist of the user 990 that corresponds to the handedness of the user 990. Additionally, in one embodiment there is a motion recognition device 910 on each wrist of the user. Also, in an embodiment a plurality of motion recognition devices 910 are used on the same wrist of a user 990 and pool the information that they gather together for analysis. For example, the motion recognition device 910 may estimate a position change of the wrist according to a motion of an elbow joint as shown in FIG. 9A, and a position change of the wrist according to a motion of a shoulder joint as shown in FIG. 9B. Such measurement is performed by using appropriate sensors included in the motion recognition device 910 whose output is used to infer motion characteristics for the motion recognition device 910.

When the motion recognition device 910 includes an acceleration sensing unit that measures acceleration with respect to six axes of movement, the motion recognition device 910, in one embodiment, additionally estimates a rotation angle and a rotational direction of the wrist from an acceleration signal with respect to six axes by inferring these estimates from the information from the acceleration sensing unit using appropriate geometrical techniques.

FIGS. 10A to 10F are diagrams illustrating a motion recognition device 1010 that detects a joint motion to recognize a motion using the gripped object, according to an example embodiment. Here, the motion recognition device 1010 estimates a joint motion of a body part related to the wrist, using an EMG signal detected by an EMG sensing unit. As discussed above, in certain embodiments an EMG signal represents certain electrical signals transmitted through skeletal muscles that are used to provide information about how body parts move.

Figure 10A:
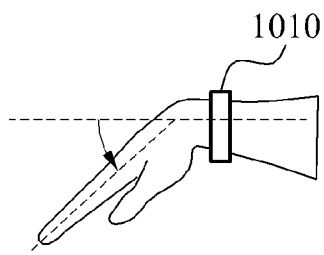
FIGS. 10A to 10G are diagrams illustrating a motion recognition device that detects a joint motion to recognize a motion using the gripped object, according to an example embodiment.
Figure 10B:
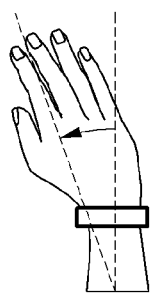
Figure 10C:
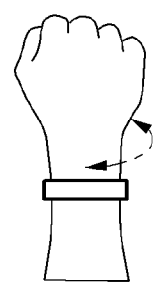

For example, the motion recognition device 1010 may estimate an up and down bending of the wrist as shown in FIG. 10A, and a degree and direction of a left and right bending of the wrist as shown in FIG. 10B. In addition, the motion recognition device 1010 may estimate a rotational direction, a rotation angle, a rotational strength of the wrist as shown in FIG. 10C. As discussed above, in an embodiment the motion recognition device 1010 receives EMG signals and interprets the EMG signals to characterize various forms of wrist movement, as illustrated in FIGS. 10A-10C.

Figure 10D:
Figure 10E:
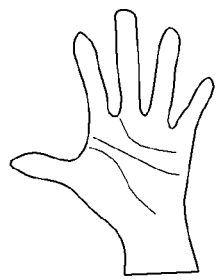
Figure 10F:
Figure 10G:
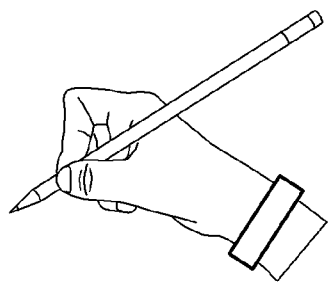

As another example, the motion recognition device 1010 may estimate a bending degree and a bending direction of a finger as shown in FIGS. 10D and 10E. As shown in FIG. 10F, a case in which the user makes a user action applying a force without bending a finger, such as tapping, may be estimated. As provided with respect to FIGS. 10A-10C, FIGS. 10D-10F illustrate various types of potential muscular activity that may be measured form EMG signals. However, instead of illustrating gross hand movements, as in FIGS. 10A-10C, FIGS. 10D-10E illustrate fine finger movements and FIG. 10F illustrates the ability of fingers to apply pressure.

According to an embodiment, the motion recognition device 1010 estimates a position of the user gripping the gripped object based on the joint motion related to the wrist, such as finger bending and wrist bending, as shown in FIGS. 9A to 10F. Also, the motion recognition device 1010 may estimate a state of the gripped object from a position of the gripped object and a position of the wrist as shown in FIG. 10G.

Figure 11:
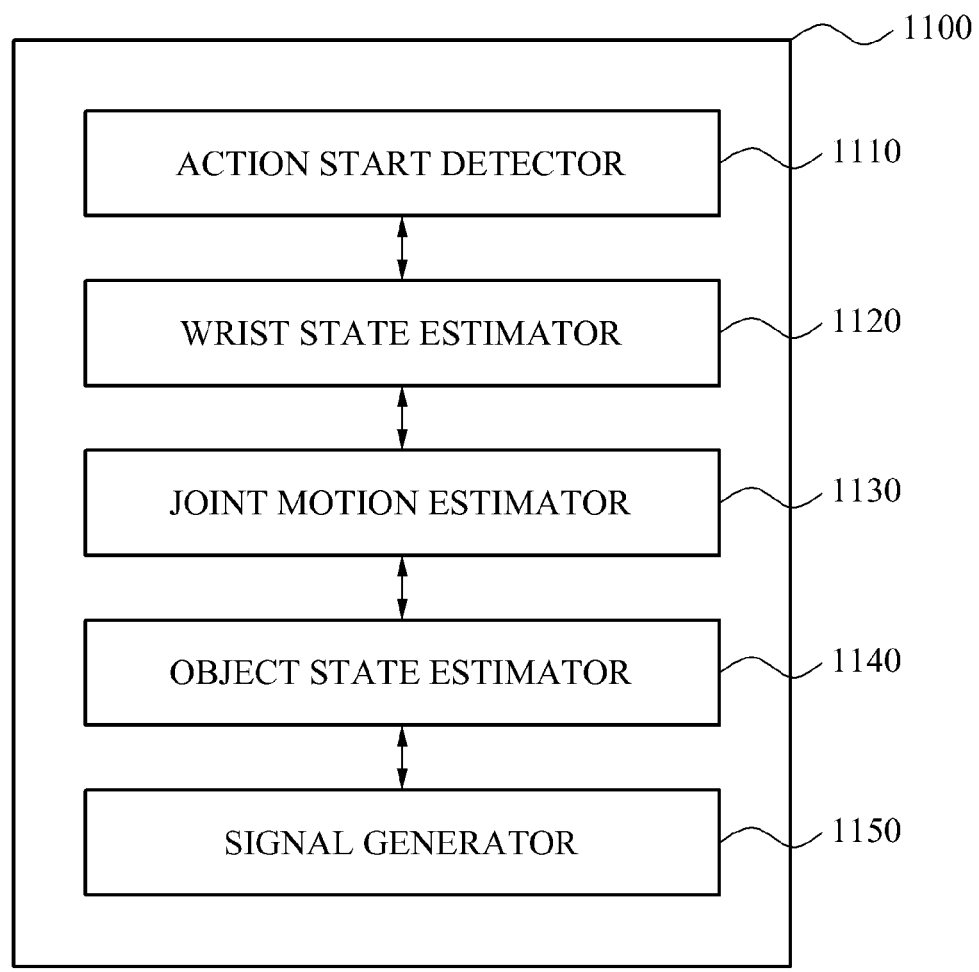
FIG. 11 is a diagram illustrating a configuration of a motion recognition device that recognizes a motion using the gripped object, according to an example embodiment.

FIG. 11 is a diagram illustrating a configuration of a motion recognition device 1100 that recognizes a motion using the gripped object, according to an example embodiment. The motion recognition device 1100 includes an action start detector 1110, a wrist state estimator 1120, a joint motion estimator 1130, an object state estimator 1140, and a signal generator 1150.

The action start detector 1110 detects the start of a writing action performed using a gripped object. In an example embodiment, action start detector 1110 includes a sound detector that detects a sound generated by the writing action, and an action start determiner that determines that the writing action has started when at least one of the sound and gripping with respect to the gripped object in a manner that indicates writing is detected. For example, the sound generated by the writing action includes a frictional sound between the gripped object and a contact surface that is interpreted to indicate that writing is detected.

The wrist state estimator 1120 estimates a state of the wrist of the user according to the writing action performed using the gripped object. In an example embodiment, the wrist state estimator 1120 includes an acceleration sensor, such as an accelerometer, to detect acceleration and movement of the wrist with respect to six axes according to the writing action, and estimate the state of the wrist, including at least one of a position change of the wrist and a rotation of the wrist, according to the acceleration.

The joint motion estimator 1130 estimates a joint motion of a body part related to the wrist, according to the writing action. The joint motion estimator 1130 optionally includes an EMG sensing unit that detects EMG of the body part related to the wrist according to the writing action, and estimate the joint motion based on the EMG. In an example embodiment, the joint motion estimator 1130 includes a gripping strength estimator to estimate the strength of a force with which the user grips the gripped object. The estimated strength may be used by a writing generator.

The object state estimator 1140 estimates the state of the gripped object according to the state of the wrist and the joint motion provided by wrist state estimator 1120 and joint motion estimator 1130. The object state estimator 1140 may include a ground surface contact estimator configured to estimate the contact position of the gripped object with respect to a ground surface, according to the state of the wrist and the joint motion, as discussed above.

The signal generator 1150 generates a control signal for controlling the external apparatus by continuously tracking the state of the gripped object. In an example embodiment, the signal generator 1150 includes a writing generator configured to generate a shape by continuously tracking the state of the gripped object. Optionally, the writing generator generates the shape derived from the state of the gripped object in a thickness corresponding to the strength of force, by continuously tracking the state of the gripped object. In some embodiments, the writing generator includes an object identifier configured to identify a type of the gripped object using at least one of an object gripping position, a sound generated by the writing action, and a voice of the user. The writing generator generates the shape by performing the action corresponding to the type of the gripped object. For example, the action corresponding to the type of the gripped object may include generating letters and sentences, and generating or correcting a drawing. Moreover, embodiments may process the contents of text or drawings to recognize these contents. For example, the text may provide a textual command or parameters for the textual command. For example, the textual command may include a command to "e-mail" and the parameter may be an e-mail address. Alternatively, embodiments may process drawings to understand the user's intentions as well, as illustrated in FIG. 8.

The signal generator 1150 transmits the control signal to at least one of an external apparatus, an input and output device, and a storage device, through a communication unit. For example, the communication unit may communicate with other apparatuses on a wired or wireless, for example through Bluetooth, Wi-Fi, Zigbee, and other communications protocols.

According to a particular embodiment, the motion recognition device 1100 further includes a biomedical signal detection unit configured to detect a biomedical signal of the user, and an object state compensator configured to adjust the estimated state to compensate for the biomedical signal by using a motion artifact according to the biomedical signal. For example, the motion recognition device 1100 extracts the motion artifact from the biomedical signal, wherein the motion artifact is generated according to the motion of the user to whom the biomedical signal detection unit is attached, and derives the corrected user action using the motion artifact. The object state compensator may use this information to compensate for the biomedical information in the state of the gripped object estimated by the object state estimation unit 1140.

For example, the biomedical signal may include information such as that obtained from electrocardiogram (ECG), electrooculogram (EOG), EMG, electroencephalogram (EEG), and similar measurements related to electrical activity in various parts of a user's body. In such an example, the motion recognition device 1100 estimates the user action by using the motion artifact extracted from the biomedical signal to improve its earlier estimates.

Figure 12:
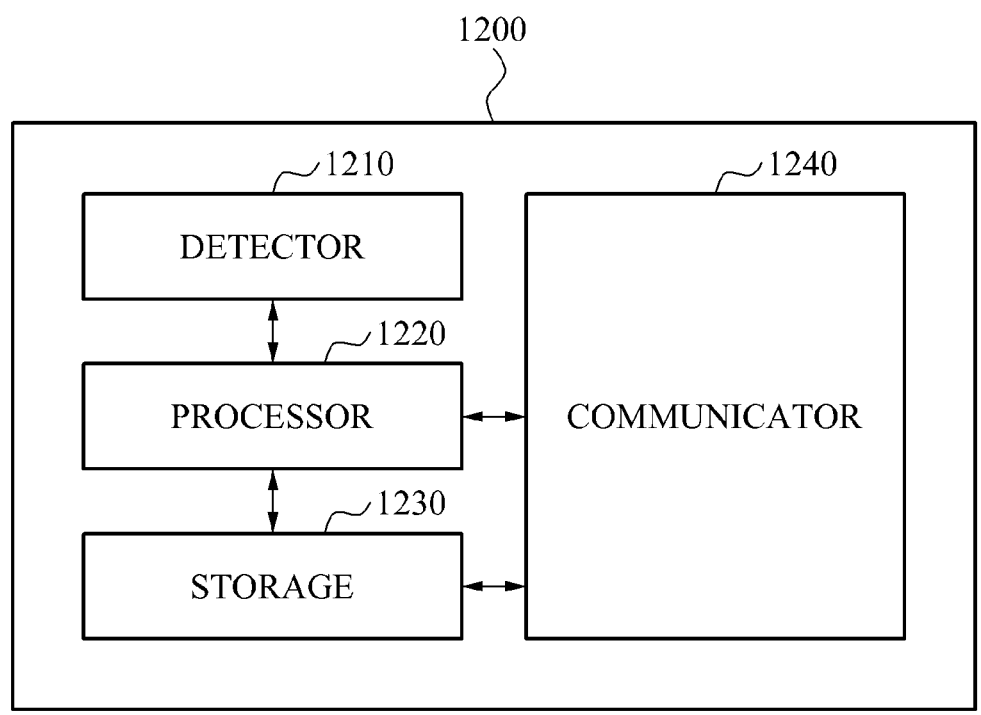
FIG. 12 is a diagram illustrating a configuration of another motion recognition device that recognizes a motion using the gripped object, according to an example embodiment.

FIG. 12 is a diagram illustrating a configuration of a motion recognition device 1200 that recognizes a motion using the gripped object, according to an example embodiment. The motion recognition device 1200 includes a detector 1210, a processor 1220, a storage 1230, and a communicator 1240.

In the example of FIG. 12, the detector 1210 detects a biomedical signal, a sound signal, and an acceleration signal. For example, the detection unit 1210 includes one or more of an EMG sensor, a sound sensor, an ECG sensor, a photoplethysmography (PPG) sensor, and an impedance sensor.

The biomedical signal includes, for example, one or more of EGC, EOG, EMG, and EEG signal information. The sound signal includes, for example, an ambient sound of the motion recognition device 1200 and a voice of the user. The acceleration signal includes, for example, a three-axis acceleration signal related to a linear motion, and a three-axis acceleration signal related to rotation with reference to each axis.

The processor 1220 performs a method of recognizing the motion using the gripped object, according to an embodiment. The processor 1210 estimates a state of the gripped object gripped by the user, using the biomedical signal, the acceleration signal, and the sound signal, and generates a control signal for controlling an external apparatus by continuously tracking the state of the gripped object. In an example, a joint motion of a body part related to the wrist is estimated from the EMG sensor, a state of the wrist is estimated from the acceleration signal, and the state of the gripped object is estimated from the state of the wrist and the joint motion. In such an example, the state of the gripped object is estimated in a similar manner to the methods described in FIGS. 3 and 4.

The storage 1230 stores at least one program including instruction words for execution of the methods described in FIGS. 3 and 4. The storage 1230 also stores a shape generated by continuously tracking the state of the gripped object.

The communicator 1240 transmits the control signal generated by the processor 1220 to the external apparatus. The communicator 1240 communicates with at least one of the external apparatus, a storage device, and an input/output device, using wired or wireless communication techniques.

In an example, the communicator 1240 wirelessly searches for the external apparatus, the storage device, and the input/output device to determine if they are available for the motion recognition device 1200.

The motion recognition device may provide a UI capable of accurately recognizing a user action such as note writing and drawing. The UI may be an intuitive and natural advanced UI not requiring a separate input and output apparatus.

According to an embodiment, the motion recognition device accurately estimates a hand motion using a biomedical signal detector, an acceleration detector, and other sources of information about the hand motion. The motion recognition device further provides an intuitive UI that responds to note writing by the user, based on the estimation of the hand motion.

According to an embodiment, the motion recognition device recognizes a large-scale motion of an arm including a hand movement of the user using an acceleration detection unit, such as an accelerometer, and estimates a user's actions of bending and stretching individual fingers and wrist motion using an EMG sensor.

According to an embodiment, when the user wearing a wrist wearable motion recognition device writes or draws on paper by a predetermined writing tool, the motion recognition device recognizes and performs the corresponding user action. While this embodiment characterizes the motion recognition device as a wrist wearable motion recognition device, other embodiments provide alternative forms for the motion recognition device.

The motion recognition device provides feedback to the user by transmitting information related to the user action to a predetermined input/output device or a storage device. For example, the input/output device may display letters, sentences, and drawings being written by the user as the user manipulates the grippable writing tool.

According to an embodiment, the motion recognition device provides an intuitive and natural writing type UI. For example, the motion recognition device may operate without a display, but may still allow an external device to be controlled. As another example, the motion recognition device may serve as a replacement for other separate equipment that would otherwise be used for inputting data. As discussed with respect to several embodiments, the user may intuitively control the external device through interaction with the motion recognition device.

According to an embodiment, the motion recognition device conveniently transmits an input of data written as part of a note to a cloud server or another local or remote storage repository. In addition, in one embodiment the motion recognition device controls the external device by drawing an icon for controlling the external device on paper or another surface and pointing at the icon to indicate a form of control for the external device.

The apparatuses and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The media may also include, alone or in combination with the software program instructions, data files, data structures, and the like. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

As a non-exhaustive illustration only, a terminal/device/unit described herein may refer to mobile devices such as, for example, a cellular phone, a smart phone, a wearable smart device (such as, for example, a ring, a watch, a pair of glasses, a bracelet, an ankle bracket, a belt, a necklace, an earring, a headband, a helmet, a device embedded in the cloths or the like), a personal computer (PC), a tablet personal computer (tablet), a phablet, a personal digital assistant (PDA), a digital camera, a portable game console, an MP3 player, a portable/personal multimedia player (PMP), a handheld e-book, an ultra mobile personal computer (UMPC), a portable lab-top PC, a global positioning system (GPS) navigation, and devices such as a high definition television (HDTV), an optical disc player, a DVD player, a Blue-ray player, a setup box, or any other device capable of wireless communication or network communication consistent with that disclosed herein. In a non-exhaustive example, the wearable device may be self-mountable on the body of the user, such as, for example, the glasses or the bracelet. In another non-exhaustive example, the wearable device may be mounted on the body of the user through an attaching device, such as, for example, attaching a smart phone or a tablet to the arm of a user using an armband, or hanging the wearable device around the neck of a user using a lanyard.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method for recognizing a motion performed using a gripped object, comprising:
    estimating a state of a wrist of a user according to a writing action performed using the gripped object;
    estimating a joint motion of a body part of the user related to the wrist according to the writing action; and
    estimating a state of the gripped object according to the state of the wrist and the joint motion,
    wherein the estimating of the joint motion comprises:
        estimating a strength of a force exerted by the user for gripping the gripped object; and
        generating a shape in a thickness corresponding to the strength of the force by continuously tracking the state of the gripped object.

2. The method of claim 1, further comprising:
    generating a control signal for controlling an external device by continuously tracking the state of the gripped object.

3. The method of claim 1, further comprising:
    detecting a start of the writing action of the user using the gripped object.

4. The method of claim 3, wherein the detecting comprises:
    determining that the writing action has started when either one or both of a sound generated by the writing action and a grip of an object corresponding to writing is detected.

5. The method of claim 1, wherein the estimating of the state of the gripped object comprises:
    estimating a contact position of the gripped object with respect to a ground surface according to the state of the wrist and the joint motion.

6. The method of claim 1, wherein the estimating of the state of the wrist comprises:
    detecting an acceleration according to the writing action; and
    estimating the state of the wrist according to the acceleration.

7. The method of claim 1, wherein the estimating a joint motion of a body part comprises:
    detecting an electrical biomedical signal corresponding to the body part related to the wrist according to the writing action; and
    estimating the join motion according to the electrical biomedical signal,
    wherein the electrical biomedical signal comprises an electrical muscle contraction signal.

8. The method of claim 1, further comprising:
    compensating for errors in the estimated state of the object using a motion artifact according to the electrical biomedical signal.

9. The method of claim 1, further comprising:
    storing the shape generated by continuously tracking the state of the gripped object.

10. The method of claim 7, wherein detecting the electrical biomedical signal comprises:
    detecting electromyogram (EMG) information of the body part related to the wrist according to the writing action as the electrical muscle contraction signal.

11. The method of claim 1, further comprising:
    identifying a type of the gripped object; and
    performing an action according to the type of the gripped object by continuously tracking the state of the object.

12. A device for recognizing a motion performed using a gripped object, comprising:
    a wrist state estimator configured to estimate a state of a wrist according to a writing action performed using the gripped object;
    a joint motion estimator configured to estimate a joint motion of a body part of the user related to the wrist according to the writing action; and
    an object state estimator configured to estimate a state of the gripped object according to the state of the wrist and the joint motion,
    the joint motion estimator comprises a gripped strength estimator configured to estimate a strength of a force extended by the user for gripping the object, and
    a writing generator is configured to generate a shape in a thickness corresponding to the strength of the force by continuously tracking the state of the gripped object.

13. The device of claim 12, further comprising:
    a signal generator configured to generate a control signal for controlling an external device by continuously tracking the state of the gripped object.

14. The device of claim 12, further comprising:
    an action start detector configured to detect a start of the writing action of the user using the gripped object.

15. The device of claim 14, wherein the action start detector comprises:
    an action start determiner configured to determine that the writing action has started when either one or both of a sound generated by the writing action and a grip of an object corresponding to writing is detected.

16. The device of claim 12, wherein the object state estimator comprises a ground surface contact estimator configured to estimate a contact position of the gripped object with respect to a ground surface according to the state of the wrist and the joint motion.

17. The device of claim 12, wherein the wrist state estimator comprises an acceleration detector configured to detect acceleration with respect to six axes according to the writing action using the gripped object, and estimate the state of the wrist including either one or both of a position change of the wrist and a rotation of the wrist according to the acceleration.

18. The device of claim 12, wherein the joint motion estimator comprises an electrical biomedical signal detector configured to detect an electrical biomedical signal corresponding to the body part related to the wrist according to the writing action and estimate the joint motion according to the electrical biomedical signal, and
    wherein the electrical biomedical signal comprises an electrical muscle contraction signal.

19. The device of claim 12, further comprising:
an object state compensator configured to compensate for errors in the estimated state of the object using a motion artifact according to the electrical biomedical signal.

20. The device of claim 12,
wherein the writing generator configured to generate the shape generated by continuously tracking the state of the gripped object.

21. The device of claim 18, wherein the electrical biomedical signal detector comprises an electromyogram (EMG) detector configured to detect EMG information generated at the body part related to the wrist according to the writing action as the electrical muscle contraction signal, and
the joint motion estimator estimates the joint motion according to the EMG information.

22. The device of claim 20, wherein the writing generator comprises an object identifier configured to identify the type of the object using any one or any combination of two or more of an object gripping position, a sound generated by the writing action, and a voice of the user, and
wherein the writing generator is further configured to generate the shape by performing the action corresponding to the type of the object.

23. A system for recognizing a motion using a gripped object, comprising:
a motion recognition device configured to estimate a state of a gripped object according to a state of a wrist of a user and a joint motion of a body part related to the wrist, and configured to transmit a control signal for controlling an external device, the control signal generated by continuously tracking the state of the gripped object; and
the external device configured to perform a predetermined operation corresponding to the control signal when receiving the control signal,
wherein the motion recognition device is further configured to estimate a strength of a force exerted by the user for gripping the object, and generate a shape in a thickness corresponding to the strength of the force by continuously tracking the state of the gripped object.

24. The system of claim 23, wherein the motion recognition device selects an external device corresponding to a shape generated by continuously tracking the state of the gripped object, and generates a signal for controlling the selected external device as the control signal.

25. The system of claim 24, wherein the control signal comprises a control command instructing the external device to perform an operation corresponding to a predetermined part of the external device when a user action that activates the predetermined part is detected from the shape.

26. A method for recognizing a motion using a gripped object, comprising:
estimating a state of a gripped object according to a state of a wrist of a user and a joint motion of a body part related to the wrist;
storing a shape generated by continuously tracking the state of the gripped object;
recognizing the shape to identify an external device corresponding to the shape and to determine an operation to be performed by the external device; and
transmitting a control signal to the external device to instruct the external device to perform the operation,
wherein the estimating the state of a gripped object comprises:
estimating a strength of a force exerted by the user for gripping the gripped object; and
generating a shape in a thickness corresponding to the strength of the force by continuously tracking the state of the gripped object.

27. The method of claim 26, wherein the shape comprises written language and the recognizing comprises recognizing the written language.

28. The method of claim 27, wherein the external device is identified based on the recognized written language.

29. The method of claim 27, wherein the operation to be performed by the external device is determined based on the recognized written language.

30. The method of claim 26, wherein the external device is identified based on recognizing that the shape represents the external device.

31. The method of claim 30, wherein a region of the shape representing the external device is a drawing of a portion of the external device that performs a designated operation, and
the transmitting of the control signal further comprises the transmitting the control signal to the external device instruct the external device to perform the designated operation in response to the user selecting the portion.

32. The method of claim 26, wherein the estimating the state of a gripped object comprises:
detecting an electrical biomedical signal corresponding to the body part related to the wrist according to a writing action; and
estimating the joint motion according to the electrical biomedical signal, and wherein the electrical biomedical signal includes a muscle contraction signal.

33. The system of claim 23, wherein the motion recognition device is further configured to detect an electrical biomedical signal corresponding to the body part related to the wrist according to a writing action, and estimate the joint motion according to the electrical biomedical signal, and
wherein the electrical biomedical signal comprises an electrical muscle contraction signal.

* * * * *